United States Patent [19]

Koppel

[11] 4,045,435

[45] Aug. 30, 1977

[54] PREPARATION OF CEPHALOSPORIN ETHERS

[75] Inventor: Gary A. Koppel, Indianapolis, Ind.

[73] Assignee: Eli Lilly and Company, Indianapolis, Ind.

[21] Appl. No.: 513,669

[22] Filed: Oct. 9, 1974

[51] Int. Cl.$^2$ .......................................... C07D 501/02
[52] U.S. Cl. ..................................... 544/28; 424/246; 544/30
[58] Field of Search .................................... 260/243 C

[56] References Cited

FOREIGN PATENT DOCUMENTS

| 7,309,136 | 1/1974 | Netherlands | 260/243 C |
|---|---|---|---|
| 7,309,137 | 1/1974 | Netherlands | 260/243 C |
| 7,309,139 | 1/1974 | Netherlands | 260/243 C |
| 734,050 | 4/1974 | South Africa | 260/243 C |

OTHER PUBLICATIONS

Ahmed et al., *Chemical Communications*, p. 1533 (1968).
Press et al., *Tetrahedron Letters*, No. 26, pp. 2677–2680, (1972).

*Primary Examiner* — Nicholas S. Rizzo
*Attorney, Agent, or Firm* — Charles W. Ashbrook; Walter E. Buting; Everet F. Smith

[57] ABSTRACT

Reaction of 3-hydroxy cephalosporins with alkylfluorosulfonates in the presence of a base provides 3-alkoxy cephalosporins which are useful as intermediates for cephalosporin antibiotic preparation.

5 Claims, No Drawings

PREPARATION OF CEPHALOSPORIN ETHERS

BACKGROUND OF THE INVENTION

The cephalosporin family of antibiotics is well known and includes a number of compounds which are now routinely used in combating infectious diseases. The cephalosporins are all characterized by having a 4-membered β-lactam ring system fused to a 6-membered dihydrothiazine ring system. The numerous cephalosporins known differ from one another primarily in the nature of the group attached to the 7-amino group and in the nature of the substituent in the 3-position. Most of the cephalosporins known to date possess a methyl or substituted methyl group in the 3-position. A new class of cephalosporins characterized by having a 3-hydroxy or 3-alkoxy group has recently been discovered and is the subject of co-pending U.S. Pat. application Ser. No. 310,191, filed Nov. 28, 1972.

This invention relates to the reaction of 3-hydroxy cephalosporin esters with alkylfluorosulfonates. Alkylfluorosulfonates are known to be potent alkylating agents, and their reactions with certain nucleophiles yield fluorosulfonic acid, one of the strongest acids known, see for example Ahmed et al. Chemical Communications, 1533 (1968). Amines, amides, esters, ethers, and sulfides readily react with alkylfluorosulfonates. Certain ketones can be converted to the corresponding enol which is then alkylated with alkylfluorosulfonates, see for example J. B. Press et al. Tetrahedron Letters, No. 26, 2677-2680, (1972).

It is an object of this invention to provide a fast, clean, and efficient etherification process of 3-hydroxy cephalosporin esters, utilizing an alkylfluorosulfonate as the alkylating agent.

SUMMARY OF THE INVENTION

This invention relates to a process for preparing cephalosporin ethers of the formula

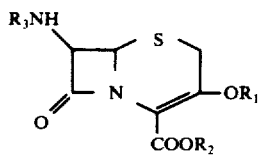

in which $R_1$ is $C_1$-$C_4$ alkyl, $R_2$ is a readily removable ester forming group, and $R_3$ is an acyl group derived from a carboxylic acid. The process provided herein comprises treating a 7-acylamido-3-hydroxy-3-cephem-4-carboxylic acid ester with a base followed by treatment with a $C_1$-$C_4$ alkylfluorosulfonate, thereby providing the corresponding 3-alkoxy cephalosporin derivative. The compounds thus prepared are useful as intermediates and can be readily converted to valuable cephalosporin antibiotics.

DETAILED DESCRIPTION OF THE INVENTION

As used herein, the term "$C_1$-$C_4$ alkyl" refers to groups such as methyl, ethyl, n-propyl, isopropyl, n-butyl, isobutyl, and the like.

Examples of a "readily removable ester forming group" include $C_4$-$C_6$ tert.-alkyl, $C_5$-$C_6$ tert.-alkenyl, $C_5$-$C_6$ tert.-alkynyl, benzyl, diphenylmethyl, p-nitrobenzyl, p-methoxybenzyl, 2,2,2-trichloroethyl, and phenacyl. Typical $C_4$-$C_6$ tert.-alkyl groups include tert.-butyl, tert.-amyl, and tert.-hexyl. Examples of $C_5$-$C_6$ tert.-alkenyl are tert.-pentenyl, and tert.-hexenyl. Typical $C_5$-$C_6$ tert.-alkynyl groups are tert.-pentynyl and tert.-hexynyl. "Readily removable ester forming groups" are well known to those skilled in the art and are recognized as groups used to protect the carboxylic acid group of a cephalosporin or penicillin during reactions of the molecule wherein the free carboxylic acid group might otherwise interfere. The methods for the introduction and removal of such carboxylic acid protecting groups are known and well documented, see for example E. Haslam in "Protective Groups in Organic Chemistry," J. F. W. McOmie, Ed., Plenum Press, New York, N.Y., Chapter 5.

In the above formula, $R_3$ represents an acyl residue of a carboxylic acid. $R_3$ includes groups having the formula

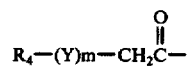

in which $R_4$ is 1,4-cyclohexadienyl, phenyl, or phenyl substituted by chlorine, bromine, fluorine, iodine, hydroxy, nitro, amino, cyano, $C_1$-$C_4$ alkyl, $C_1$-$C_4$ alkoxy; Y is O or S, and $m$ is 0 or 1. Typical examples of such acyl groups include 3-chlorophenylacetyl, 3-fluorophenylacetyl, p-hydroxyphenylacetyl, 1,4-cyclohexadienylacetyl, phenoxyacetyl, 4-aminophenoxyacetyl, 3-cyanophenylthioacetyl, 2-propylphenylacetyl, 3-butoxyphenylthioacetyl, 3-ethoxyphenoxyacetyl, 4-bromophenylthioacetyl, phenylthioacetyl, 3-iodophenylthioacetyl, 4-nitrophenoxyacetyl, 2-methylphenylthioacetyl, 4-isobutoxyphenylacetyl, 3-ethylphenoxyacetyl, 4-tert.-butylphenylacetyl, 4-cyanophenoxyacetyl, 2-chlorophenylthioacetyl, 3-iodophenoxyacetyl, 2-isopropylphenylacetyl, 2-cyanophenylacetyl, and the like.

$R_3$ is additionally an acyl group of the formula

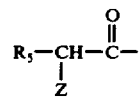

wherein $R_5$ is $R_4$ as defined hereinabove, 2-thienyl or 3-thienyl; and Z is protected hydroxy or protected amino. Examples of such groups include
α-(2-thienyl)-α-tert.-butoxycarbonylaminoacetyl;
α-formyloxy-α-(4-acetoxyphenyl)acetyl;
α-isobutyloxycarbonylamino-α-(2-thienyl)acetyl;
α-furfuryloxycarbonylamino-α-(3-thienyl)acetyl;
α-acetoxy-α-phenylacetyl;
α-cyclohexyloxycarbonylamino-α-(2-ethoxyphenyl)acetyl;
α-benzyloxy-α-(3-cyanophenyl)acetyl;
α-(4-methoxybenzyloxycarbonylamino)-α-(4-chlorophenyl)acetyl;
α-furfuryloxycarbonylamino-α-(3-cyanophenyl)acetyl;
α-diphenylmethoxycarbonylamino-α-(4-isobutoxyphenyl)acetyl;
α-benzoyloxy-α-(3-methylphenyl)acetyl;
α-p-nitrobenzoyloxy-α-(2-thienyl)acetyl;
α-trifluoroacetoxy-α-(3-nitrophenyl)acetyl;
α-chloroacetoxy-α-(4-isopropoxyphenyl)acetyl;
α-methoxyacetoxy-α-(3-thienyl)acetyl;

α-ethoxycarbonyloxy-α-(2-fluorophenyl)acetyl; and related groups.

R₃ is additionally a heteroarylacetyl group of the formula

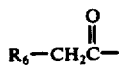

in which R₆ is 2-thienyl, 3-thienyl, 2-furyl, 3-furyl, 5-tetrazolyl, 2-thiazolyl, or 2-oxazolyl.

All of the above defined acyl groups are well known to those skilled in the cephalosporin art and are thoroughly documented in the patent literature, see for example U.S. Pat. Nos. 3,641,021; 3,665, 003; 3,644,347; 3,767,655 and 3,759,905.

The term "protected" when used in reference to "protected amino" refers to any of a number of typical amino protecting groups such as alkoxycarbonyl groups, especially tert.-butoxycarbonyl, isobutoxycarbonyl, 2,2,2-trichloroethoxycarbonyl, or the enamine obtained from methylacetoacetate. Similarly, "protected hydroxyl" refers to common groups used to protect a hydroxyl group during a chemical reaction. Hydroxyl groups are typically protected by conversion to the formate or acetate ester. All of these amino and hydroxyl protecting groups are well known and routinely used, and are described in detail by J. W. Barton and C. B. Reese in "Protective Groups in Organic Chemistry," J. F. W. McOmie, Ed., Plenum Press, New York, N.Y., 1973, Chapters 2 and 3 respectively.

It will be understood that during the process of this invention, groups that are known to react with alkylfluorosulfonates, such as amino, hydroxyl, or carboxyl groups for instance, will be suitably protected to preclude unwanted side reactions. The process provided herein can be carried out on 3-hydroxy cephalosporins which have unprotected reactive groups in the side-chain portion of the molecule; however, lower yields of the desired 3-alkoxy derivative are generally observed. Alternatively, the process of this invention can be carried out on cephalosporins having side chains not requiring protection, such as phenoxyacetyl or 2-thienylacetyl for example, and subsequently cleaving such a side chain and re-acylating with a different acyl group. These side-chain cleavages and subsequent re-acylations are well known procedures.

In the process of the present invention, a 3-hydroxy cephalosporin is alkylated by treatment with a non-hydroxylic base and an alkylfluorosulfonate to provide the corresponding 3-alkoxy cephalosporin. Typical alkylfluorosulfonates commonly utilized include methyl fluorosulfonate, ethyl fluorosulfonate, isopropyl fluorosulfonate, and the like. Any of a number of strong non-hydroxylic bases can be incorporated in the reaction. Typical strong bases commonly used include alkali metal amides, such as sodium amide, lithium diethylamide, lithium diisopropylamide, potassium amide; alkali metal hydrides, for example sodium hydride, potassium hydride, or lithium hydride; and alkali metal alkoxides, such as lithium methoxide, potassium ethoxide, sodium isopropoxide, potassium tert.-butoxide, sodium dimethylethylmethoxide, and the like. Additionally, strong non-hydroxylic bases such as triphenylmethyl lithium, triphenylmethyl sodium, triphenylmethyl potassium, butyl lithium, phenyl lithium, sodium dimsyl, and the like can be used. An especially preferred base in potassium tert.-butoxide.

The 3-hydroxy cephalosporin, the base, and the alkylfluorosulfonate are generally employed in approximately equimolar quantities, although an excess of either reactant can be used in desired. The reaction is best carried out in a unreactive solvent. Any of a number of unreactive solvents can be employed in the present process. An "unreactive solvent" as used herein refers to solvents which do not substantially react with the alkylfluorosulfonate. Typical solvents generally used include amides such as hexamethylphosphortriamide or dimethylacetamide, or sulfoxides such as dimethyl sulfoxide or diethyl sulfoxide, or ethers such as diethyl ether, diisopropyl ether, or dioxane. Hexamethylphosphortriamide is an especially preferred solvent for the present process. The etherification reaction is best carried out at a temperature below 30° C., for example between −50° C. and 30° C., and is preferably carried out at about −20° C. to about 15° C. The reaction is generally substantially complete within about 10 to about 90 minutes, and is routinely curtailed after about 30 to 45 minutes. The product ether can be isolated by diluting the reaction mixture with a water immiscible solvent, such as ethyl acetate, chloroform, benzene, or the like, and subsequently washing the organic solution free of reaction solvent, excess base, or excess alkylating agent, for example by repeated washings with water. Removal of the solvent from the organic solution containing the product then affords the 3-alkoxy cephalosporin. Further purification is generally not needed; however, standard procedures such as chromatography or crystallization can be utilized if desired for further purification of the product.

As hereinbefore indicated, a starting material required for the present process is a 7-acylamido-3-hydroxy-3-cephem-4-carboxylic acid ester. These 3-hydroxy compounds are prepared by treating a 7-acylamido-3-exomethylene cephalosporin ester with ozone to form an intermediate ozonide which on decomposition, affords a 3-hydroxy cephalosporin. Alternatively, a 7-amino-3-exomethylenecepham-4-carboxylic acid ester is treated with ozone, and the ozonide so formed is decomposed to provide a 7-amino-3-hydroxy-3-cephem-4-carboxylic acid ester, which ester can then be acylated under known conditions to provide the corresponding 7-acylamido-3-hydroxy-3-cephem-4-carboxylic acid ester.

More particularly, a 3-exomethylene cephalosporin, which compound is prepared as described by Chauvette et al., J. Org. Chem., 38, 2994 (1973), is treated with ozone at a temperature of about −50° C., generally in a solvent such as methanol, ethyl acetate, or dichloromethane. The ozonolysis of the 3-exomethylene group is halted as soon as the ozonide formation is complete, as evidenced for example by this layer chromatography, thereby precluding oxidation of the sulfur atom of the dihydrothiazine ring system. Once the ozonide of the 3-exomethylene cephalosporin is formed, a mild reducing agent, such as sodium bisulfite or sulfur dioxide, is added to the reaction mixture thereby decomposing the intermediate ozonide to provide the corresponding 3-hydroxy cephalosporin. The 3-hydroxy cephalosporin is then converted to the corresponding 3-alkoxy derivative by the procees of this invention.

Examples of 3-alkoxy cephalosporins prepared by the process of this invention include:
2,2,2-trichloroethyl 7-phenoxyacetamido-3-methoxy-3-cephem-4-carboxylate;

tert.-butyl 7-(2-thienylacetamido)-3-ethoxy-3-cephem-4-carboxylate;

p-methoxybenzyl 7-(α-tert.-butoxycarbonylamino-α-phenyl)acetamido-3-n-propoxy-3-cephem-4-carboxylate;

2-(2-methyl-3-butenyl) 7-(α-formyloxy-α-phenyl)acetamido-3-isopropoxy-3-cephem-4-carboxylate;

p-nitrobenzyl 7-(α-benzyloxycarbonylamino-α-phenyl)acetamido-3-n-butoxy-3-cephem-4-carboxylate;

diphenylmethyl 7-phenoxyacetamido-3-isobutoxy-3-cephem-4-carboxylate;

tert.-butyl 7-(α-acetoxy-α-2-thienyl)acetamido-3-methoxy-3-cephem-4-carboxylate; and the like.

As hereinbefore indicated, the 3-alkoxy cephalosporin esters prepared by the process of this invention are useful as intermediates for the preparation of 3-alkoxy cephalosporin acids which are valuable antibiotics. For example, a tert.-butyl 7-phenoxyacetamido-3-($C_1$-$C_4$ alkoxy)-3-cephem-4-carboxylate can be converted to the 4-carboxylic acid antibiotic. Alternatively, the 7-phenoxyacetyl group can be removed by standard methods to provide the corresponding 7-amino-3-alkoxy-3-cephem-4-carboxylate, which can be reacylated if desired with any of a number of acyl groups known to impart antibacterial activity ot cephalosporin nuclei.

In order to further illustrate the process of this invention, the following detailed examples are presented. The particular aspects presented in the following examples should not, however, be construed as limiting the invention in any respect.

EXAMPLE 1 p-Nitrobenzyl 7-(2-thienylacetamido)-3-methoxy-3-cephem-4-carboxylate

A solution of 56 mg. of potassium tert.-butoxide in 8 cc. of hexamethylphosphortriamide (HMPA) was stirred under a nitrogen atmosphere and cooled to 0° C. in an ice-water bath. A solution of 247 mg. of p-nitrobenzyl 7-(2-thienylacetamido)-3-hydroxy-3-cephem-4-carboxylate in 4 cc. of HMPA was added in one portion to the cold reaction mixture, following which a solution of 0.09 cc. of methyl fluorosulfonate was added in one portion. The reaction mixture was stirred at 0° C. for 30 minutes, and then poured into 50 cc. of ethyl acetate. The ethyl acetate solution was washed five times with 20 cc. portions of water, dried, and the solvent was removed under reduced pressure to provide 130 mg. of p-nitrobenzyl 7-(2-thienylacetamido)-3-methoxy-3-cephem-4-carboxylate.

nmr ($CDCL_3$): δ3.41 (s, 2H, C-2 methylene). δ3.82 (s, 2H, side-chain methylene). δ3.84 (s, 3H, C-3 methoxyl). δ5.08 (d, 1H, C-6). δ5.38 (q. 2H, ester methylene). δ5.60 (m, 1H, C-7).

EXAMPLE 2 tert.-butyl 7-(α-tert.-butoxycarbonylamino-α-phenyl)-acetamido-3-ethoxy-3-cephem-4-carboxylate.

To a cold solution of 505 mg. of tert.-butyl 7-(α-tert.-butoxycarbonylamino-α-phenyl)acetamido-3-hydroxy-3-cephem-4-carboxylate in 20 cc. of HMPA containing 70 mg. of sodium ethoxide is added 116 mg. of ethyl fluorosulfonate in one portion. The reaction mixture was stirred at about 0° C. for 35 minutes, and then poured into 50 cc. of dichloromethane. The organic solution was washed five times with 20 cc. portions of water, dried, and the solvent was removed therefrom under reduced pressure, affording tert.-butyl 7-tert.-butoxycarbonylamino-α-phenyl)acetamido-3-ethoxy-3-cephem-4-carboxylate.

EXAMPLE 3

Diphenylmethyl 7-(4-chlorophenylthio)acetamido-3-methoxy-3-cephem-4-carboxylate

A solution of 60 mg. of lithium diisopropylamide in 10 cc. of HMPA is cooled to 0° C. and 260 mg. of diphenylmethyl 7-(4-chlorophenylthio)acetamido-3-hydroxy-3-cephem-4-carboxylate is added in one portion. After stirring the reaction mixture for 1 minute, 70 mg. of methyl fluorosulfonate is added, and stirring is continued for 30 minutes. The reaction mixture is poured into 50 cc. of ethyl acetate, washed with water, and dried. Removal of the solvent under reduced pressure provides diphenylmethyl 7-(4-chlorophenylthio)acetamido-3-methoxy-3-cephem-4-carboxylate.

I claim:

1. A process for preparing a cephalosporin ether of the formula

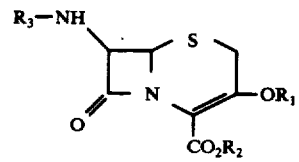

wherein:
$R_1$ is $C_1$-$C_4$ alkyl;
$R_2$ is a readily removable ester forming group; and
$R_3$ is a carboxylic acid acyl residue selected from the group consisting of

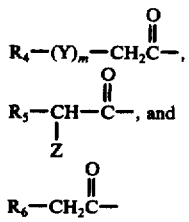

wherein:
$R_4$ is 1,4-cyclohexadienyl, phenyl, or phenyl substituted by chlorine, bromine, fluorine, iodine, hydroxy, nitro, amino, cyano, $C_1$-$C_4$ alkyl, $C_1C_4$ alkoxy, Y is O or S, and m is zero or one;
$R_5$ is $R_4$, 2-thienyl, or 3-thienyl;
Z is protected hydroxy or protected amino;
$R_6$ is 2-thienyl, 3-thienyl, 2-furyl, 3-furyl, 5-tetrazolyl, 2-thiazolyl, or 2-oxazolyl;
comprising treating a 7-acylamido-3-hydroxy-3-cephem-4-carboxylic acid ester with a non-hydroxylic base selected from the group consisting of alkali metal amides, alkali metal hydride, alkali metal alkoxides, alkali metal triphenylmethides, butyl lithium, phenyl lithium, and sodium dimsyl, and a $C_1$-$C_4$ alkylfluorosulfonate in an unreactive organic solvent.

2. The process according to claim 1 wherein the solvent is hexamethylphosphortriamide.

3. The process according to claim 2 wherein the base is potassium tert.-butoxide.

4. The process according to claim 2 wherein the alkylfluorosulfonate is methylfluororsulfonate.

5. The process according to claim 2 wherein the alkylfluorosulfonate is ethylfluorosulfonate.

* * * * *